United States Patent [19]
Pettit et al.

[11] Patent Number: 5,196,447
[45] Date of Patent: Mar. 23, 1993

[54] NERISTATIN 1

[75] Inventors: George R. Pettit, Paradise Valley; Feng Gao, Tempe, both of Ariz.

[73] Assignee: Arizona Board of Regents, a body Corporate of The State of Arizona, Acting on behalf of Arizona State University, Tempe, Ariz.

[21] Appl. No.: 742,609

[22] Filed: Aug. 8, 1991

[51] Int. Cl.$^5$ ............... C07D 493/22; A61K 31/365
[52] U.S. Cl. ............................... 514/450; 549/267
[58] Field of Search ..................... 549/267; 514/450

[56] References Cited

U.S. PATENT DOCUMENTS 4,560,774 12/1985 Pettit et al. ............................ 549/267
4,611,066 9/1986 Pettit et al. ............................ 549/267
4,833,257 5/1989 Pettit et al. ............................ 549/267

Primary Examiner—C. Warren Ivy
Assistant Examiner—A. A. Owens
Attorney, Agent, or Firm—Richard R. Mybeck

[57] ABSTRACT

The marine bryozoan *Bugula neritina* has been found to contain a novel 22-membered macrocyclic lactone which is an inhibitor of lymphocytic leukemia as measured by the US National Cancer Institute's P 388 and in vitro evaluation system. The novel lactone is herein denominated "neristatin 1" and is elucidated.

4 Claims, No Drawings

NERISTATIN 1

Partial funding for the work reported herein was provided by the National Cancer Institute Grant No. CA-44344-01A1, National Cooperative Drug Discovery Grants AI-25696-02 and -03, U.S. Army Medical Research and Development Command Grant DAMD17-89-Z-9021 and National Institute of Health Marine Grant CA-16049-11-12. The United States government has certain rights in this invention.

INTRODUCTION

The present invention relates to the discovery and isolation of a new substance found in Bugula neritina specimens collected from the Gulf of Mexico and herein denominated "Neristatin 1". Neristatin 1 is an inhibitor of lymphocytic leukemia as measured by the National Cancer Institute P388 cell line. The new substance has the structural formula:

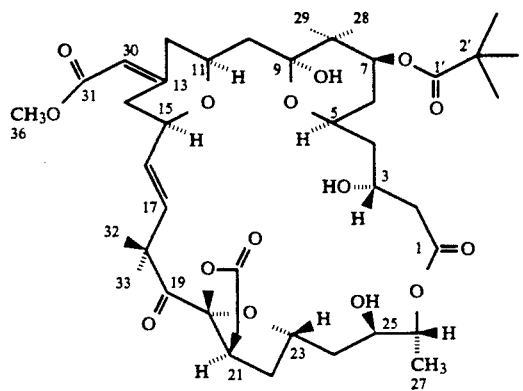

BACKGROUND OF THE INVENTION

The marine bryozoan Bugula neritina has been found to contain a unique series of closely related macrocyclic (22-membered) lactones known as bryostatins. Because of their very selective antineoplastic and cytostatic activity, potent influence on protein kinase C biochemical pathways, anti-tumor promoter effects and stimulation of bone marrow progenitor cells to form colonies (GM-CSF activity), bryostatin 1 has been selected for clinical evaluation. Discovery and study of a bryostatin biosynthetic precursor or degradation products has been considered necessary to gain further mechanistic and structure/activity insights. The isolation and structural elucidation of the first such substance, herein designated "neristatin 1", is described herein.

BRIEF SUMMARY OF THE INVENTION

The present invention relates to the discovery of a unique precursor or degradation product of a bryostatin showing antineoplastic and cytostatic activity. Neristatin 1 has been isolated from a bryozoan, Bugula neritina, found in the Gulf of Mexico and its structure has been elucidated by X-ray crystallographic structural analysis and 2D-NMR studies.

Accordingly, a principal object of the present invention is to isolate and elucidate a new natural substance which has appreciable protein Kinase C affinity, is active against the P388 murine lymphocytic leukemia cell line, and provides the bryostatin biosynthetic precursor or degradation product necessary to gain further mechanistic, structure and activity insights into the bryostatin series.

Another object of the present invention is to isolate and elucidate a novel macrocytic lactone herein denominated "neristatin 1" derived from the naturally occurring marine bryozoan, Bugula neritina.

These and still further objects a shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

A 1,000 kg (approximate damp wt.) recollection (1986, Gulf of Mexico Coast of Florida) of Bugula neritina Linnaeus was extracted with 2-propanol. Initial solvent partitioning and steric exclusion chromatographic procedures were conducted as previously described for the closely related Bryozoan Amathia convolute (See:Pettit et al., Tetrahedron. 1985,41,985). Separation was guided by bioassay employing the P388 lymphocytic leukemia cell line with a combination of gel permeation (and partition on SEPHADEX LH-20) and partition (SILICA GEL) chromatography, high speed countercurrent distribution and HPLC techniques to provide 8.0 mg($8.0 \times 10^{-2}$% yield) of colorless neristatin 1: mp 214°-216° D.; $[\alpha]_D = +98°$ ($CH_2Cl_2$, c=0.26; $R_f$ (SILICA GEL) 0.62 (tolueneethyl ethyl acetate-methanol 3:1:1); HPLC retention times, 11 min. (RP C-8 column, 10 mm×25 cm, 80% methanol-water, 0.8 mL/min) and 9 min (normal phase column, 10.0 mm×25 cm, hexane-methylene chloride-methanol 14:8:1 with UV detection at λ=254 nm); HRFABMS (with LiI) found 799.4090, calc. for $C_{41}H_{60}O_{15}Li$ 799.4092; and EIMS 70 eV, m/z, M+792 (33) calc. 792 for $C_{41}H_{60}O_{15}$, 774 (100%) [M-$H_2O$]S+S and 756 (8%) [774-$H_2O$]S+S. The $^1H$- and $^{13}C$-and HMBC-NMR values for this substance now follows.

The NMR $^1H$-, $^{13}C$, and HMBC assignments for neristatin 1 in deuteriochloroform solution now follows: $^1H$(400MHz): 2.72 (dd, 3.7,13, H-2a), 2.37 (dd,11,13, H-2b), 4.35 (m, became ddd, 3.7,11,11 upon the addition of $D_2O$; H-3), 1.84; 1.38 (m, H-4a,b), 3.67 (m, H-5), 1.65; 1.50 (m, H-6a,b), 4.81 (dd, 5,12, H-7), 2.08 (brd, 13, H-10a), 2.04 (dd, 11,13, H-10b), 3.85 (brt, 11, H-11), 2.29 (brt, 12, H-12a), 2.11 (brd, 12, H-12b), 4.00 (brd, 15, H-14a), 1.90 (brdd, 14,15, H-14b), 3.95 (brdd, 6,14, H-15), 5.63 (dd, 6,15.8, H-16), 6.42 (d, 15.7, H-17), 3.54 (ddd, 11,7.1,7.1 H-21), 1.82; 1.72 (m, H-22a,b), 4.69 (brddd, 5,10.5,11, H-23), 1.52; 1.38 (m, H-24a,b), 3.47 (ddd, 6.5,9.7,9.7, became t, 9.7, following addition of $D_2O$, H-25), 4.87 (dq, 9.7,6.5, H-26), 1.09 (d, 6.5, H-27), 0.94; 0.95 (s, H-28,29), 5.82 (brs, H-30), 1.28; 1.27 (s, H-32,33), 2.87 (dd, 11,18.5, H-34a), 2.40 (dd, 7,18.5, H-34b), 3.70 (s, OMe), 1.16 (s, H-3',4',5'), 6.09 (s, C-9 OH), 4.92 (d, 6.3, C-25 OH). $^{13}C$(100MHz): 169.13 (C-1), 44.87 (C-2), 66.27 (C-3), 42.94 (C-4), 66.50 (C-5), 32.94 (C-6), 73.62 (C-7), 42.31 (C-8), 101.52 (C-9), 35.42 (C-10), 74.93 (C-11), 42.08 (C-12), 155.52 (C-13), 36.18 (C-14), 77.80 (C-15), 127.50 (C-16), 136.40 (C-17), 47.99 (C-18), 203.32 (C-19), 115.20 (C-20), 40.41 (C-21), 37.24 (C-22), 77.70 (C-23), 38.25 (C-24), 71.58 (C-25), 73.86 (C-26), 16.93 (C-27), 20.94 (C-28), 14.71 (C-29), 115.20 (C-30), 166.87 (C-31), 24.83 (C-32), 26.71 (C-33), 34.19 (C-34), 174.19 (C-35), 51.16 (C-36, OMe), 178.00 (C-1'), 39.00 (C-2'), 27.11 (C-3',4',5'). HMBC(500MHz): H2a to C-1, C-3; H-7 to C-29; H-12a to C-11, C-13, C-30; H-12b to C-13, C-30; H-14a to C-12, C-13, C-15; H-15 to C-11, C-12, C-13; H-17 to C-15, C-18, C-19, C-32; H-28 to C-7, C-8, C-9, C-29; H-29 to C-7, C-8, C-9, C-28; H-30 to C-12, C-14, C-31; H-32 to C-17, C-18, C-19, C-33; H-33 to C-17, C-18, C-19, C-32; H-34a to C-21, C-20, C-35; H-34b to C-35; H-36 to C-31; H-3'-5' to C-1', C-2'; C-9 OH to C-8, C-9, C-10.

The possibility of a relationship between neristatin 1 and the bryosatins was first suggested by the color displayed by neristatin 1 on a thin layer chromatographic plate. However, a detailed 2D NMR study rapidly uncovered major structural differences between the substances. Only one methoxy signal appeared in the $^1$H NMR spectrum and signals assigned using $^1$H-$^1$H COSY and $^1$H-$^{13}$C correlated spectra demonstrated that neristatin 1 did not possess a bryopyran ring. Furthermore, in the $^1$H NMR spectrum, the H-26 signal was shifted downfield at $\delta$ 4.87 and the H-25 signal shifted upfield at $\delta$ 3.47 compared with those of the bryostatins. More importantly, a doublet signal at $\delta$ 4.92 (J=6.3 Hz) was found coupled with the H-25 signal. The former disappeared and the later was simplified upon addition of $D_2O$. Such evidence suggested that a free hydroxy group was present at C-25 and that lactonization was involved at the C-26 position. From the downfield shifts of the H-17 signal to $\delta$ 6.42, the H-32 and H-33 methyl signals to $\delta$ 1.28 and 1.27 combined with a $^{13}$C signal at $\delta$ 203.32, a carbonyl group was assigned to C-19.

The presence of four 13C ester carbonyl signals at $\delta$ 169.13, 166.87, 174.19 and 178.00 combined with results of heteronuclear band correlation (HMBC) experiments also supported presence of a $\nu$-lactone. The two signals at $\delta$ 40.41 (C-21). Furthermore, the C-20 to C-23 region of neristatin 1 proved refractory to rigorous 2D NMR interpretation until the crystal structure analysis was in hand.

Unlike the generally stable bryostatins (except for bryostatin 3), neristatin 1 demonstrated sensitivity to recrystallization attempts and a number of small samples rapidly degraded in various solvents until it recrystallized unchanged from acetone-hexane. While only relatively poor quality (cracked, vapor pockets and other imperfections) crystals were available for the crystal structure determination, this difficulty was surmounted and an unequivocal structure was obtained for neristatin 1 as shown below. The best crystal (dimensions $\approx 0.18 \times 0.30 \times 0.40$ mm) was mounted on the end of a glass capillary. Data with very poor intensities (and markedly broadened reflections—average can angle 2.30°) was collected to a maximum of $2\Theta = 140°$ on an ENRAF-NONIUS CAD-4 diffractometer at $-65°$ C. One octant of data was collected for the orthorhombic crystal, space group $P2_12_12_1$, with a=23.325(9), b=16.368(3), c=11.149(14), V=4256.7$^3$, $\rho_c$=1.237 g cm$^{-3}$ for Z=4. Insufficient sample was available for an accurate density measurement. The $\omega/2\Theta$ scan technique was used with graphite monochromated Cu Ka radiation ($\lambda$1.5418Å). Following measurement of each reflection, the FRIEDEL equivalent reflections were merged and systematic absences rejected. A total of 5845 unique reflections remained, of which 2907 ((Fo). 5$\sigma$(Fo) containing FRIEDELS) were used in the subsequent structure refinement. Direct methods was used in the structure determination.

Initial application of SHELXS-86, using the default starting values, provided a complete structure containing 56 nonhydrogen atoms. The structure was consistent with the high field NMR data and allowed logical interpretation of the refractory (by NMR) C-20 to C-23 region. Subsequent isotropic refinement of the structure (containing 56 nonhydrogen atoms and 60 hydrogens calculated at optimum positions and allowed to ride) with SHELXTL-PLUS provided conventional and weighted residual indices of R=0.148 and $R_w$=0.146, respectively. Based on the relatively poor data and low reflection/parameter ratio, these refinement results were not unexpected. The tendency of a number of atoms to yield "nonpositive definite" thermal parameters precluded anisotropic refinement. Although results of the single crystal X-ray analysis were considered marginal, the structure assigned neristatin 1, as shown below, was considered unequivocal and quite consistent with the extensive NMR correlations and assignments reported above. Bond lengths and angles obtained for the crystal structure of neristatin 1 fell within generally accepted limits, except for the $C_{14}$-$C_{15}$ bond, which was longer that expected (1.71 Å). The absolute stereochemical configuration assigned to neristatin 1, as shown, is based upon the known absolute stereochemistry of the related bryostatins. Stereochemical assignments for the ten chiral centers of neristatin 1 are as follows: 3(R), 5,(R), 7(S), 9(S), 15(R), 20(S), 21(S), 23(S), 25(R), 26(R).

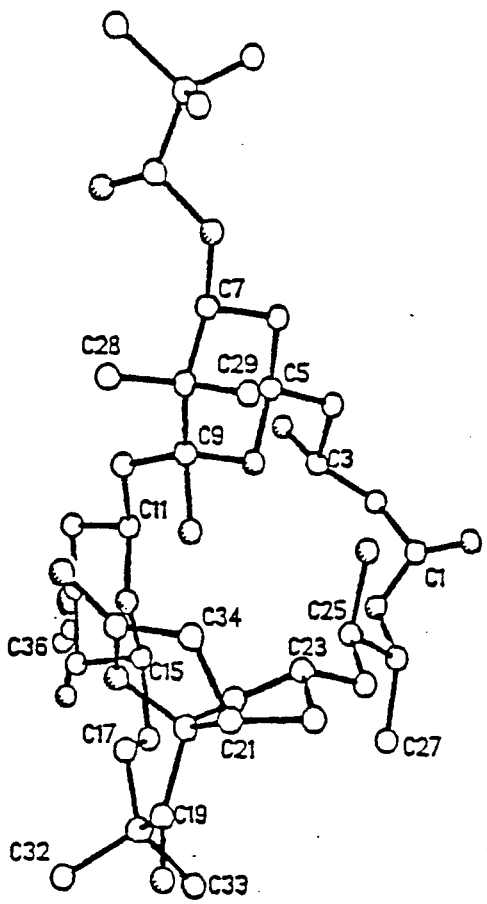

Protein kinase C is the target for the bryostatins. The binding affinity of neristatin 1 for protein kinase C was determined by competition for [26-$^3$H] bryostatin 4 binding, using the conditions previously developed for measurement of highly potent bryostatins. Under these conditions, which involve reconstitution of the enzyme in phosphatidylserine/TRITION X-100 mixed micelles, the $K_i$ for neristatin 1 was 124±10nM (mean±SEM, 4 experiments), compared to 1.3 nM for bryostatin 4 and 12.3 nM for the typical phorbol 12,13-dibutyrate. Because of the relatively low affinity of neristatin 1, it was also assayed under the usual phorbol ester binding conditions using reconstitution of protein kinase C in phosphatidylserine. Here, the $K_i$ of neristatin 1 was 21.2±1.3 nM (mean±sem, 3 experiments), compared to 0.53 nM phorbol 12,13-dibutyrate. Under these conditions, the 26-epimer of bryostatin 4 has a $K_d$ of 13 nM. The foregoing demonstrates that neristatin 1 retains appreciable affinity for protein kinase C, albeit an order of magnitude less than that of phorbol 12,13-dibutyrate and at least two orders of magnitude less than that of bryostatin 4.

Consistent with the binding results, neristatin 1 was active ($ED_{50}$10 μg/mL) against the P388 cell line. The reduced but still significant potency of neristatin compared to the bryostatin 5 was considered a considerable asset for further defining structure/activity relationships and biochemical mechanisms among this remarkable series of biosynthetic products.

The significance of the NCI screens and their relationship to ultimate human therapy is well-known in the art. (See: Boyd, Status of the NCI preclinical antitumor drug discovery screen: implications for selection of new agents for clinical trial In: DeVita et al, CANCER: *Principals and Practices of Oncology, update series.* Vol. 3., No. 10, Lippincott, Philadelphia, 1989, ppl-12; and Boyd et al, Data display and analysis strategies from NCI disease oriented in vitro antitumor drug screen. In: Valeriote et al, *Antitumor Drug Discovery and Develoṃment,* Kluwer Academic Press, Amsterdam, 1990)

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A compound denominated neristatin 1 having the structural formulae:

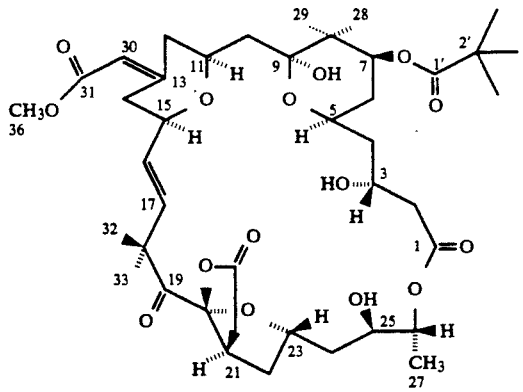

2. A method of inhibiting cell growth in NCI's P388 Murine lymphatic leukemia cell line comprising treating said leukemia with a cell growth inhibiting amount of neristatin 1.

3. A compound isolated from *Bugula neritina* and having, in deuteriochloroform solution, the following NMR, $^1$H-, $^{13}$C and HMBC assignments:

$^1$H(400MHz); 2.72 (dd, 3.7,13, H-2a), 2.37 (dd,11,13, H-2b), 4.35 (m, became ddd, 3.7,11,11 upon the addition of $D_2O$: H-3), 1.84; 1.38 (m, H-4a,b), 3.67 (m, H-5), 1.65; 1.50 (m, H-6a,b), 4.81 (dd, 5,12, H-7), 2.08 (brd, 13, H-10a), 2.04 (dd, 11,13, H-10b), 3.85 (brt, 11, H-11), 2.29 (brt, 12, H-12a), 2.11 (brd, 12, H-12b), 4.00 (brd, 15, H-14a), 1.90 (brdd, 14,15, H-14b), 3.95 (brdd, 6,14, H- 15), 5.63(dd, 6,15.8, H-16), 6.42 (d, 15.7, H-17), 3.54 (ddd, 11,7.1,7.1 H-21), 1.82; 1.72 (m, H-22a,b), 4.69 (brddd, 5.10.5,11, H-23), 1.52; 1.38 (m, H-24a,b), 3.47 (ddd, 6.5,9.7,9.7, became t, 9.7, following addition of $D_2O$, H-25), 4.87 (dq, 9.6,6.5, H-26), 1.09 (d, 6.5, H-27), 0.94; 0.95 (s, H-28,29), 5.82 (brs, H-30), 1.28; 1.27 (s, H-32,33), 2.87 (dd, 11,18.5, H-34a), 2.40 (dd, 7,18.5, H-34b), 3.70 (s, OMe), 1.16 (s, H-3',4',5'), 6.09 (s, C-9 OH), 4.92 (d, 6.3, C-25OH). $^{13}$C(100MHz): 169.13 (C-1), 44.87 (C-2), 66.27 (C-3), 42.94 (C-4), 66.50 (C-5), 32.94 (C-6), 73.62 (C-7), 42.31 (C-8), 101.52 (C-9), 35.52 (C-10), 74.93 (C-11), 42.08 (C-12), 155.52 (C-13), 36.18 (C-14), 77.80 (C-15), 127.50 (C-16), 136.40 (C-17), 47.99 (C-18), 203.32 (C-19), 115.20 (C-20), 40.41 (C-21), 37.24 (C-22), 77.70 (C-23), 38.25 (C-24), 71.58 (C-25), 73.86 (C-26), 16.93 (C-27), 20.94 (C-28), 14.71 (C-29), 115.20 (C-30), 166.87 (C-31), 24.83 (C-32), 26.71 (C-33), 34.19 (C-34), 174.19 (C-35), 51.16 (C-36, OMe), 178.00 (C-1'), 39.00 (C-2'), 27.11 (C-3',4',5'). HMBC(500MHZ): H2a to C-1, C-3; H-7 to C-29; H-12a to C-11, C-13, C-30; H-12B to C-13, C-30; H-14a to C-12, C-13, C-15; H-15 to C-11, C-12, C-13; H-17 to C-15, C-18, C-19, C8-32; H-28 to C-7, C-8, C-9, C-29; H-29 to C-7, C-8, C-9, C-28; H-30 to C-12, C-14, C-31; H-32 to C-17, C-18, C-19, C-33; H-33 to C-17, C-18, C-19, C-32; H-34a to C-21, C-20, C-35; H-34B to C-35; H-36 to C-31; H-3'-5' to C-1', C-2'; C-9 OH to C-8, C-9, C-10.

4. A method of inhibiting cell growth in NCI's P388 Murine lymphatic leukemia cell line comprising treating said leukemia with a cell growth inhibiting amount of a compound according to claim 3.

* * * * *